United States Patent [19]

Tang et al.

[11] Patent Number: 5,668,268
[45] Date of Patent: Sep. 16, 1997

[54] PASSIVATED POLYMER SUPPORTS FOR NUCLEIC ACID SYNTHESIS

[75] Inventors: Jin-Yan Tang, Shrewsbury; Jimmy X. Tang, Framingham, both of Mass.

[73] Assignee: Hybridon, Inc., Cambridge, Mass.

[21] Appl. No.: 562,841

[22] Filed: Nov. 27, 1995

[51] Int. Cl.$^6$ .............................. C07H 21/04; C12Q 1/68
[52] U.S. Cl. .......................... 536/25.3; 435/6; 536/25.4; 536/25.6
[58] Field of Search .................... 435/6; 536/25.3, 536/25.4, 25.6; 514/44

[56] References Cited

U.S. PATENT DOCUMENTS

| | | | |
|---|---|---|---|
| 4,638,032 | 1/1987 | Benner | 525/54.11 |
| 5,470,463 | 11/1995 | Girot et al. | 210/198.2 |

OTHER PUBLICATIONS

Reddy et al. Tetrahedron Letters 35(32): 5771–5774 1994.

*Primary Examiner*—Stephanie W. Zitomer
*Assistant Examiner*—Paul B. Tran
*Attorney, Agent, or Firm*—Hale and Dorr LLP

[57] ABSTRACT

The invention provides passivated organic polymer supports, processes for their preparation and processes for their use in oligonucleotide synthesis that allow for highly efficient solid phase synthesis of oligonucleotides.

8 Claims, 1 Drawing Sheet

PASSIVATED POLYMER SUPPORTS FOR NUCLEIC ACID SYNTHESIS

BACKGROUND OF THE INVENTION

1. Field of the Invention

The invention relates to the chemical synthesis of oligonucleotides and to materials and processes that are useful in such synthesis.

2. Summary of the Related Art

Oligonucleotides have become indispensable tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, Curr. Op. in Biotech. 6:12 (1995); and *Antisense Research and Applications* (Crooke and Lebleu, Eds., CRC Press, Boca Raton, 1993). Early synthetic approaches included phosphodiester and phosphotriester chemistries. Khorana et al., J. Molec. Biol. 72:209 (1972) discloses phosphodiester chemistry for oligonucleotide synthesis. Reese, Tetrahedron Lett. 34:3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, Tetrahedron Lett. 22:1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, Tetrahedron Lett. 28:3539–3542 (1987), teaches synthesis of oligonucleotide methylphosphonates using phosphoramidite chemistry. Connolly et al., Biochemistry 23:3443 (1984), discloses synthesis of oligonucleotide phosphorothioates using phosphoramidite chemistry. Jager et al., Biochemistry 27:7237 (1988), discloses synthesis of oligonucleotide phosphoramidates using phosphoramidite chemistry. Agrawal et al., Proc. Natl. Acad. Sci. USA 85, 7079–7083 (1988), discloses synthesis of oligonucleotide phosphoramidates and phosphorothioates using H-phosphonate chemistry.

Solid phase synthesis of oligonucleotides by any of the known approaches ordinarily involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleoside linkages are formed between the 3' functional group (e.g., phosphoramidite group) of the incoming nucleoside and the 5' hydroxyl group of the 5'-most nucleoside of the nascent, support-bound oligonucleotide.

Refinement of methodologies is still required, however, particularly when making a transition to large-scale synthesis (10 μmol to 1 mmol and higher). See Padmapriya et al., Antisense Res. Dev. 4:185 (1994). Several modifications of the standard phosphoramidite methods have already been reported to facilitate the synthesis and isolation of oligonucleotides. See e.g., Padmapriya et al., supra; Ravikumar et al., Tetrahedron 50:9255 (1994); Theisen et al., Nucleosides & Nucleotides 12:43 (1994); and Iyer et al., Nucleosides & Nucleotides 14:1349 (1995) (Kuijpers et al., Nucl. Acids Res. 18:5197 (1990); and Reddy et al., Tetrahedron Lett. 35:4311 (1994).

One limitation in solid phase synthesis resides in the nature of the solid phase support upon which the oligonucleotide is synthesized. A variety of solid support materials have been described for solid phase oligonucleotide synthesis, the most prevalent of which is controlled-pore glass (CPG). (See, e.g., Pon, Methods in Molec. Biol. 20:465 (1993)). Unfortunately, CPG suffers certain limitations that prevent it from being an ideal support material. See e.g., Ron et al., Biotechniques 6:768 (1988); McCollum et al., Nucleosides and Nucleotides 6:821 (1987); Bardella et al., Tetrahedron Lett. 31:6231–6234 (1990) For example, CPG is unstable under the standard ammonium hydroxide procedure that is used to deprotect the oligonucleotide and to cleave it from the solid support. In addition, oligonucleotide synthesis using CPG as the solid support results in rather high levels of n–1 contaminant in the synthesis product.

To overcome these problems, various attempts have been made to develop polymer supports to replace CPG. See e.g., Gao et al., Tetrahedron Lett. 32:5477–5479 (1991); *The Gene Assembler*™, *A Fully Automated DNA Synthesizer*, Pharmacia Fine Chemicals, Uppsala, Sweden (1986). The use of organic supports in this context has been explored. Reddy et al., Tetrahedron Lett. 35:5771–5774 (1994) discloses an organic support based on native Fractogel ("Toyopearl", TosoHaas, Philadelphia, Pa.). Fractogel, however, has inherent limitations as a support for oligonucleotide synthesis, due to its low density when packed in acetonitrile and its limited pore volume per unit bed volume. Although it would be desirable to replace CPG with a support that lacks its limitations, none of the polymer supports developed to date have provided the efficiency that CPG provides.

There is, therefore, a need for polymer supports for oligonucleotide synthesis that provide the efficiency of CPG, but that do not suffer from the instability or n–1 contamination problems inherent in CPG.

BRIEF SUMMARY OF THE INVENTION

The invention provides passivated organic polymer supports, processes for their preparation and processes for their use in oligonucleotide synthesis that allow for highly efficient solid phase synthesis of oligonucleotides. The efficiency of synthesis provided when using the organic polymer supports according to the invention is at least as good as that provided by controlled pore glass (CPG). Unlike CPG, the organic polymer supports according to the invention are highly stable under standard ammonium hydroxide conditions used to deprotect the oligonucleotides and to cleave them from the solid support. In addition, solid phase oligonucleotide synthesis using the organic polymer supports according to the invention results in greatly reduced production of n–1 contaminant oligonucleotide.

In a first aspect, the invention provides a passivated organic polymer support for solid phase synthesis of oligonucleotides. The passivated organic polymer support according to the invention comprises a plurality of microscopic particles. Each particle has amino and/or hydroxyl groups covalently bound to the particle. Each particle further has nucleosides covalently bound to some of the amino and/or hydroxyl groups. At least some of the amino and/or hydroxyl groups that are not covalently bound to nucleosides are covalently bound to hydrophobic passivating groups.

In a second aspect, the invention provides a process for passivating an organic polymer support for oligonucleotide synthesis. The process according to the invention comprises introducing hydrophobic passivating groups at the site of free amino and/or hydroxyl groups that are covalently bound to the particles that comprise the organic polymer support. Organic polymer supports for oligonucleotide synthesis have amino and/or hydroxyl groups covalently bound to the particles that comprise the support. Some of the amino and/or hydroxyl groups are covalently bound to nucleosides, while others remain as free amino and/or hydroxyl groups. The presence of these amino and/or hydroxyl groups lends a hydrophilic character to the particles. In the process according to the invention, the hydrophilic character of the particles is reduced by covalently attaching hydrophobic passivating groups to the amino and/or hydroxyl groups. Passivation of the particles in this manner results in greatly improved efficiency of oligonucleotide synthesis.

In a third aspect, the invention provides an improved process for solid phase oligonucleotide synthesis. In this improved process according to the invention, the improvement comprises carrying out solid phase synthesis on the passivated organic polymer support according to the invention. This process of oligonucleotide synthesis according to the invention produces oligonucleotides at least as efficiently as processes utilizing CPG, but with greatly reduced contamination by n–1 and without chemical breakdown of the solid support.

The organic polymer supports and process for their use according to the invention are useful for synthesizing oligonucleotides on a scale ranging from small laboratory scale to large commercial scale. Thus, the organic polymer supports and process for their use according to the invention can be used to supply oligonucleotides for research purposes, for diagnostic purposes and for therapeutic purposes using the antisense approach.

BRIEF DESCRIPTION OF THE DRAWINGS

FIG. 1A shows the surface before addition of the nucleosides. FIG. 1B shows the surface after addition of the nucleosides. FIG. 1C shows the surface after passivation with benzoyl groups. DMT represents a dimethoxytrityl group.

DETAILED DESCRIPTION OF THE PREFERRED EMBODIMENTS

Figure 1A:
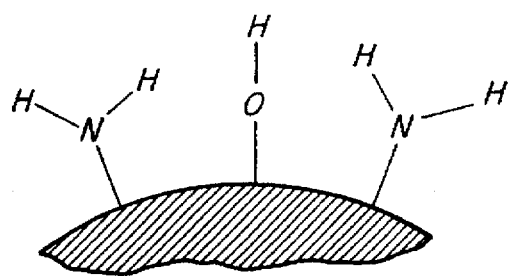
FIGS. 1A, 1B and 1C show a surface area within a pore of a particle that comprises an organic polymer support according to the invention.

The invention relates to the chemical synthesis of oligonucleotides and to materials and processes that are useful in such synthesis. The patents and publications identified in this specification are within the knowledge of those skilled in this field and are hereby incorporated by reference in their entirety.

The invention provides passivated organic polymer supports, processes for their preparation, and processes for their use in oligonucleotide synthesis that allow for highly efficient solid phase synthesis of oligonucleotides. The efficiency of synthesis provided when using the organic polymer supports according to the invention is at least as good as that provided by controlled pore glass (CPG). Unlike CPG, the organic polymer supports according to the invention are highly stable under standard ammonium hydroxide conditions used to deprotect the oligonucleotides and to cleave them from the solid support. In addition, solid phase oligonucleotide synthesis using the organic polymer supports according to the invention results in greatly reduced production of n–1 contaminant oligonucleotide.

In a first aspect, the invention provides an organic polymer support for solid phase synthesis of oligonucleotides. The organic polymer support according to the invention comprises a plurality of passivated organic polymer microscopic particles. Preferably, the particles are generally spherical and are from about 10 microns to about 100 microns in diameter. In a particularly preferred embodiment, the particles are from about 20 to about 60 microns in diameter. Preferably, the particles are porous, to increase the surface area available for oligonucleotide attachment and synthesis. Preferably, the pore size range is from about 50 to about 4000 angstroms, as measured by mercury porosimetry. Most preferably, the pore size is from about 200 to about 500 angstroms. An example of a particularly preferred prepassivation particle is the Toyopearl® AF AMINO-550F particle produced by TosoHaas (Philadelphia, Pa). This particle is a copolymer of methacrylate and ethylene glycol, has a pore size of about 300 angstroms, a mean diameter of 20–60 microns, a density of 0.36 g/ml after swelling in acetonitrile and a pore volume of 0.54 ml/1 ml of bed volume.

The material for the base particle is preferably a polymer or copolymer comprising acrylate, methacrylate or polystyrene. Preferred copolymers include, but are not limited to, methacrylate/ethylene glycol (Toyopearl, TosoHaas, Philadelphia, Pa.), dimethacrylate/pentaerythritol, polystyrene/divinylbenzene, copolymers of pentaerythritol dimethacrylate and a methacrylate monomer, copolymers of a hydrophilic monomer selected from the group consisting of hydroxyalkyl methacrylates, aminoalkyl methacrylates, N-vinylpyrrolidone, acrylonitrile, methacrylonitrile, acrylic acid, methacrylic acid, and mixtures thereof, with a substantially hydrophobic monomer selected from the group consisting of ethylene dimethacrylate, ethylene diacrylate, methylenebisacrylamide, diethylene glycol methacrylamide, poly (ethyleneglycol) methacrylamide, neopentyl glycol diacrylate, neopentyl glycol dimethacrylate, trimethylol propane trimethacrylate, divinylbenzene, and mixtures thereof, copolymers of polar monomers such as hydroxyalkyl acrylates and hydroxyalkyl methacrylates, with non-polar monomers such as alkyl acrylates and methacrylates, together with cross-linking agents such as alkylene diacrylates and methacrylates, and homopolymers of pentaerythritol dimethacrylate. These and other appropriate organic polymers are known in the art and can be synthesized by art recognized techniques, such as those taught in U.S. Pat. Nos. 4,224,415, 4,256,840, 4,297,220, 4,501,816, 4,246,362, 4,184,020, 4,135,892 and 3,925,267, each of which is hereby incorporated by reference.

Each particle has amino groups and/or hydroxyl groups covalently bound to the particle surface, including surface areas within the pores. For purposes of the invention, any area which is at, attached to, or within the particle boundary and in fluid communication with an extraparticle area is considered to be a part of the particle surface. Amino and/or hydroxyl functionalization of organic polymer particles is well known in the art, and is described, for example in U.S. Pat. Nos. 4,245,005 and 5,030,352, each of which is hereby incorporated by reference. In addition, such amino and/or hydroxyl functionalized particles are commercially available from several sources, including TosoHaas (Philadelphia, Pa.) and Merck (Darmstadt, Germany).

Figure 1B:
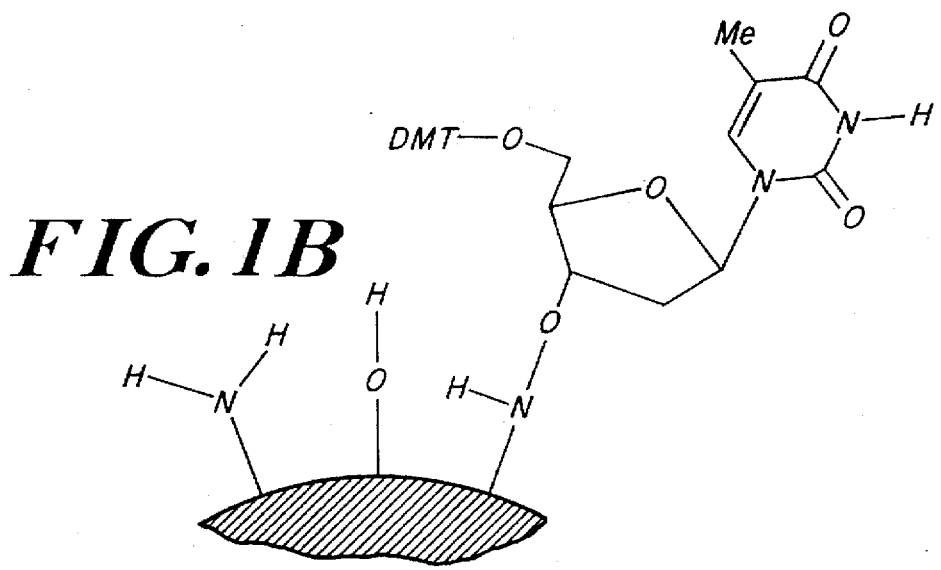

Each particle further has nucleosides covalently bound to some of the amino and/or hydroxyl groups. Loading of the nucleosides onto the particles can be carried out as described herein, or by any of the procedures that are well known in the art (see e.g., Reddy et al., Tetrahedron Lett. 35:5771–5774 (1994); Bhongle et al., Synthetic Communications 25:3671–3679 (1995)). However, at high nucleoside loading densities, it is not possible to have every amino and/or hydroxyl group bound to a nucleoside. Consequently, some of the amino and/or hydroxyl groups will remain free, which imparts a hydrophilic character to the particle surface. An example of this is illustrated in FIG. 1B.

Figure 1C:
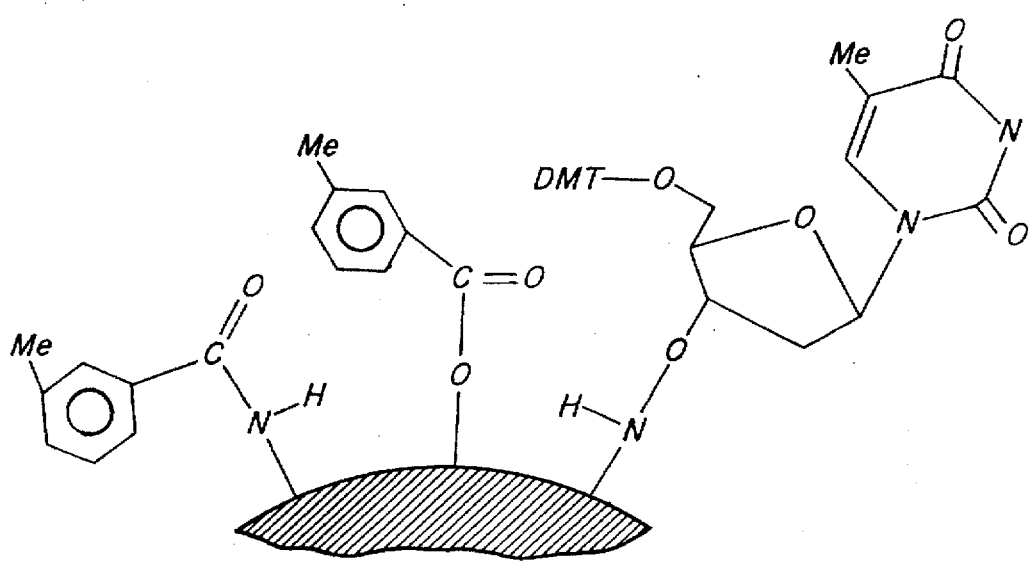

A unique feature of organic polymer particles according to the invention is that they are passivated, i.e., at least some of the amino and/or hydroxyl groups that are not covalently bound to nucleosides are covalently bound to hydrophobic passivating groups, such as aroyl groups. Preferred aroyl groups for polymer supports according to this aspect of the invention include those having the structure I:

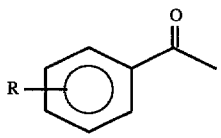

wherein there are from 0 to 3 R groups and each R group is independently a lower alkyl group, a phenyl group, a halogen, or a nitro group. Passivation with such a structure reduces the hydrophilic character of the particle surface. The surface of one embodiment of such a particle is illustrated in FIG. 1C. Preferably, of the amino and/or hydroxyl groups that are not covalently bound to nucleosides, from about 50 per cent to about all of such groups are covalently bound to a hydrophobic passivating group, and most preferably from about 90% to about all.

In a second aspect, the invention provides a process for passivating an organic polymer support for oligonucleotide synthesis. The process according to the invention comprises introducing hydrophobic passivating groups, such as aroyl groups, at the site of free amino and/or hydroxyl groups that are covalently bound to the particles that comprise the organic polymer support. Preferred aroyl groups for the process according to this aspect of the invention include those having the structure I:

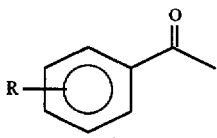

wherein there are from 0 to 3 R groups and each R group is independently a lower alkyl group, a phenyl group, a halogen, or a nitro group.

Organic polymer supports for oligonucleotide synthesis have amino and/or hydroxyl groups covalently bound to the particles that comprise the support. Some of the amino and/or hydroxyl groups are covalently bound to nucleosides, while others remain as free amino and/or hydroxyl groups. The presence of these amino and/or hydroxyl groups lends a hydrophilic character to the particles. In the process according to the invention, the hydrophilic character of the particles is reduced by covalently attaching hydrophobic passivating groups, such as aroyl groups to the amino and/or hydroxyl groups. Preferably, from about 50 per cent to about all of such amino and/or hydroxyl groups are covalently bound to a hydrophobic passivating group, and most preferably from about 90% to about all. Passivation of the particles in this manner results in greatly improved efficiency of oligonucleotide synthesis.

The process according to this aspect of the invention comprises contacting an organic polymer support particle having a surface that has both covalently bound nucleosides and covalently bound free amino and/or hydroxyl groups with an appropriate passivating reagent. An appropriate passivating reagent is a reagent that is capable of causing a hydrophobic passivating group, such as an aroyl group, to become covalently linked to free amino and/or hydroxyl groups on the surface of the particle. Preferred passivating reagents include acid anhydrides of aroyl groups or aroyl chlorides including acid anhydrides or aroyl chlorides of aroyl groups having the structure I:

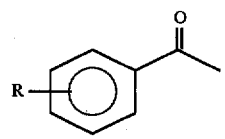

wherein there are from 0 to 3 R groups and each R group is independently a lower alkyl group, a phenyl group, a halogen, or a nitro group. In one particularly preferred embodiment of the process according to this aspect of the invention, the passivating reagent is a mixture comprising benzoic anhydride and dimethylaminopyridine.

In a third aspect, the invention provides an improved process for solid phase oligonucleotide synthesis. In this improved process according to the invention, the improvement comprises carrying out solid phase synthesis on the passivated organic polymer support according to the invention. In certain preferred embodiments of the process according to this aspect of the invention, such synthesis is carried out using the phosphoramidite, H-phosphonate, or phosphotriester approach. This process of oligonucleotide synthesis according to the invention produces oligonucleotides at least as efficiently as processes utilizing CPG, but with greatly reduced contamination by n-1 byproduct and without chemical breakdown of the solid support.

The organic polymer supports and process for their use according to the invention are useful for synthesizing oligonucleotides on a scale ranging from small laboratory scale to large commercial scale. Thus, the organic polymer supports and process for their use according to the invention can be used to supply oligonucleotides for research purposes, for diagnostic purposes and for therapeutic purposes using the antisense approach.

The following examples are intended to further illustrate certain preferred embodiments of the invention and are not intended to be limiting in nature.

EXAMPLE 1

Nucleoside Derivatization and Passivation of Organic Polymer Solid Supports

A mixture of hydroxybenzotriazole (0.1 g), 1,3-diisopropylcarbodiimide (1 ml) and 5% pyridine/acetonitrile (100 ml) was hand shaken until a clear solution was obtained. To the solution was added 20 g dried AF AMINO-550F organic polymer beads derivatized with amino groups to an amino group density of 244–400 micromoles/g (Toyopearl, TosoHaas, Philadelphia, Pa.). Next, 1.5 g DMT-thymidine succinic acid was added and the mixture was shaken in an orbital shaker at 170 rpm for about six hours at room temperature. The mixture was then filtered with a Buchner funnel and the beads were washed five times with 100 ml 5% pyridine/ acetonitrile. A solution of 15 g benzoic anhydride and 3 g dimethylaminopyridine in 100 ml 20% pyridine/acetonitrile was added and the mixture was shaken in an orbital shaker at 170 rpm overnight at room tempera- 200:342–346 (1992)) and capillary gel electrophoresis (Andrus, In *Methods in Molecular Biology*, Vol. 26, Agrawal (Ed.), 1994, pp. 277–300). Phosphate content was determined by ion exchange chromatography (Bergot and Egan, J. Chromatog. 35:599 (1992).

The results are shown in Table I, below.

TABLE I

Synthesis of GEM91 Using Polymer Support

| Synthesis No. | Loading | 'BA' treated | IEX (%) | PO (%) | CE (n) (%) | CE (n-1) (%) |
|---|---|---|---|---|---|---|
| 134-48 | 98.6 umole/g | No | 39.0% | 1.0% | 38.0% | 5.4% |
| 134-91 | 77.3 umole/g | No | 25.7% | 1.3% | NA | NA |
| 134-64 | 74.4 umole/g | Yes | 78.1% | 0.4% | 80.0% | 1.8% |
| 134-44 | 88.2 umole/g | Yes | 78.7% | 0.46% | 79.7% | 1.8% |
| 134-50 | 88.2 umole/g | Yes | 79.4% | 0.36% | 77.5% | 3.3% |
| 134-62 | 134.4 umole/g | Yes | 67.4% | 0.33% | 73.5% | 2.1% |
| 134-33(CPG) | 82.0 umole/g | NA | 78.8% | 0.40% | 66.8% | 5.2% | ture. The mixture was then filtered in a Buchner funnel and washed five times with 100 ml 5% pyridine/ acetonitrile. Next, the beads were treated with a solution of 10% acetic anhydride, 10% N-methylimidazole, 20% pyridine in tetrahydrofuran overnight at room temperature. The mixture was filtered in a Buchner funnel and washed five times in 100 ml acetonitrile +100 ml methylene chloride, then the beads were vacuum dried overnight. The level of nucleoside loading was determined using a conventional DMT cation assay (Gait, *Oligonucleotide Synthesis, A Practical Approach*, p. 107, IRL Press (1984). After swelling in acetonitrile, the passivated beads were found to be approximately 10% denser than the beads prepared according to Example 2 below.

EXAMPLE 2

Nucleoside Derivatization of Organic Polymer Solid Supports Without Passivation To prepare unpassivated organic polymer solid supports as a control for the effect of passivation, the procedure of Example 1 was carried out, except that the step of adding the benzoic anhydride and dimethylaminopyridine and the subsequent shaking were omitted.

EXAMPLE 3

Synthesis of Oligonucleotides

To test the effectiveness of various solid support materials for oligonucleotide synthesis, the following synthesis were performed. In each synthesis, the same oligonucleotide phosphorothioate was prepared. The oligonucleotide chosen for the synthesis was GEM®-91, a well characterized oligonucleotide complementary to the translation initiation region of the human immunodeficiency virus gag gene (see Agrawal and Tang, Antisense Research and Development 2:261–266 (1992)). All syntheses were conducted on an OligoPilot™ II synthesizer (Pharmacia Biotech, Uppsala, Sweden) with a 12 ml fixed bed column. In all syntheses, standard cyanoethyl phosphoramidites were used in 1.5 fold excess. All syntheses were carried out on 300 to 400 micromole scale.

Synthesis products were tested for purity by ion exchange chromatography (Metelev and Agrawal, Anal. Biochem.

These results demonstrate that at similar nucleoside loading levels, oligonucleotide synthesis carried out on organic polymer supports according to the invention is at least as efficient as similar synthesis carried out on CPG. Moreover, these results show that synthesis carried out on organic polymer supports according to the invention results in greatly reduced contamination with n–1 byproduct. In addition, these results demonstrate that synthesis using passivated support particles according to the invention is far more efficient than similar synthesis using unpassivated organic polymer support particles.

Those skilled in the art will recognize that many equivalents to the products and processes according to the invention can be made by making insubstantial changes to such products and processes. The following claims are intended to encompass such equivalents.

What is claimed is:

1. An organic polymer support for solid phase synthesis of oligonucleotides, such support comprising a plurality of passivated organic polymer microscopic particles, wherein each particle has amino groups and/or hydroxyl groups covalently bound to the particle surface, wherein each particle further has nucleosides covalently bound to some of the amino and/or hydroxyl groups, and wherein at least some of the amino and/or hydroxyl groups that are not covalently bound to nucleosides are covalently bound to a hydrophobic passivating group, wherein the hydrophobic passivating group is an aroyl group.

2. The polymer support according to claim 1, wherein the particles are from about 10 microns to about 100 microns in diameter.

3. The polymer support according to claim 2, wherein the particles are porous, having a pore size range from about 50 to about 4000 angstroms.

4. The polymer support according to claim 3, wherein the particles are from about 20 to about 60 microns in diameter and have a pore size range from about 200 to about 500 angstroms.

5. The polymer support according to claim 4, wherein the aroyl group is a benzoyl group.

6. The polymer support according to claim 5, wherein the particles are a copolymer of methacrylate and ethylene glycol.

7. An improved process for solid phase oligonucleotide synthesis, the improvement comprising carrying out the solid phase oligonucleotide synthesis on a passivated organic polymer support according to claim 1.

8. A process for passivating an organic polymer support for oligonucleotide synthesis, such progress comprising contacting an organic polymer support particle having a surface that has covalently bound free amino and/or hydroxyl groups and nucleosides covalently bound to the support via said amino and/or hydroxyl groups with a hydrophobic passivating reagent, wherein the passivating reagent is an acid anhydride of an aroyl group or an aroyl chloride.

* * * * *